United States Patent [19]

Castelli et al.

[11] 4,453,541
[45] Jun. 12, 1984

[54] ATHLETIC SUPPORTER

[76] Inventors: Joseph T. Castelli, 2415 Willowbrook Rd., Pittsburgh, Pa. 15241; Maccalleen C. Desmet, Cecil, Pa. 15321

[21] Appl. No.: 424,424

[22] Filed: Sep. 27, 1982

Related U.S. Application Data

[63] Continuation of Ser. No. 196,607, Oct. 14, 1980, abandoned.

[51] Int. Cl.³ ............................................... A61F 5/40
[52] U.S. Cl. .................................... 128/158; 128/159; 128/160
[58] Field of Search .................... 128/132 R, 158, 159, 128/160, 138 R

[56] References Cited

U.S. PATENT DOCUMENTS

| 1,230,665 | 6/1917 | Butterly | 128/158 |
| 1,250,407 | 12/1917 | Woods | 128/158 |
| 1,381,254 | 6/1921 | Thorp | 128/160 |
| 1,421,077 | 6/1922 | Goldsmith | 128/160 |
| 1,641,094 | 8/1927 | Peterkin | 128/158 |
| 2,266,062 | 12/1941 | Montmarquet | 128/160 |
| 2,623,210 | 12/1952 | Chatfield | 128/159 |
| 2,717,388 | 9/1955 | Rutledge | 128/159 |
| 3,310,053 | 3/1967 | Greenwood | 128/132 R |
| 3,526,221 | 9/1970 | Garber | 128/132 R |
| 3,909,847 | 10/1975 | Holt et al. | 128/132 R |

Primary Examiner—C. Fred Rosenbaum
Assistant Examiner—C. W. Shedd
Attorney, Agent, or Firm—Stanley J. Price, Jr.; John M. Adams

[57] ABSTRACT

An athletic supporter includes a waistband with a pair of leg straps each attached at one end to the waistband and at the opposite end to an elastic mesh protective enclosure which is held in position to provide groin protection on a human body. The protective enclosure includes overlying inner and outer layers of elastic mesh material sewn together to form a closed end portion connected to the end of the straps and an open upper end portion where the inner layer is sewn to the waistband. The inner layer forms a pouch for supporting the groin region in one application of use of the athletic supporter. In another application of use the protective enclosure is adapted to receive a protective cup which is held in position to protect the groin region of the body against impact blows. An elastic strap is sewn to the open upper end portion of the protective enclosure with the ends of the elastic strap sewn to the waistband. Stretching the waistband stretches the elastic strap into abutting overlapping relation with the waistband to close the open upper end portion of the protective enclosure and thereby maintain the cup in a stabilized position on the groin region.

5 Claims, 5 Drawing Figures

ATHLETIC SUPPORTER

CROSS REFERENCE TO RELATED APPLICATIONS

This application is a continuation of copending application Ser. No. 196,607 filed on Oct. 14, 1980, now abandoned, entitled "Athletic Supporter" by Joseph T. Castelli and Mac Calleen C. Desmet.

BACKGROUND OF THE INVENTION

1. Field of the Invention

This invention relates to a protective support device and more particularly to an athletic supporter having a protective enclosure that is adapted to receive a cup to be worn with the athletic supporter in one application of use and is adapted in an another application of use to support the groin region of the wearer without a cup when participating in strenuous work or athletic activity that does not require cup protection.

2. Description of the Prior Art

Devices and garments for protecting portions of the human body against injury during strenuous work and athletic activity are well known in the art. The most commonly known garments are the athletic supporter and the protective cup which are both used to provide different degrees of protection for the groin region of the male body from impact. The athletic supporter or jock strap is primarily used to support the groin region and the protective cup is used to protect the groin region from injury due to impact blows.

The conventional athletic supporter is most commonly associated with "light" athletic activity, such as gym-type athletic activity that does not involve bodily contact or use of a projectile. On the other hand, the protective cup is used in the body contact sports, such as football, hockey, rugby, soccer, and other sports that utilize a projectile to avoid injury by blows inadvertently directed to the groin region of the participant.

Examples of known protective devices that provide cup protection are disclosed in U.S. Pat. Nos. 2,283,684; 3,176,686; 3,229,692; 3,314,422; 3,788,314; and 4,043,329. Generally the cup protector is molded from a semi-rigid material or a rigid plastic material such as polypropylene or polyethylene as disclosed in the U.S. Pat. No. 4,134,400. Also the cup protector may be constructed of foam rubber and foam is also used to line the peripheral edge of the cup and make the cup more comfortable and non-irritating when worn.

The protective cup must be supported in a manner to cover the area of the body to be protected and to remain in the desired position during physical activity of the wearer. This may be accomplished by a number of methods where the cup is inserted as a separate element between the body of the wearer and the athletic garment. For example, U.S. Pat. No. 3,229,692 discloses a separable protective insert adapted to be worn by the wearer under tight trunks or shorts in contact with the groin area.

The protector cup disclosed in the U.S. Pat. No. 3,788,314 is freely inserted within a pouch that is formed integral with an athletic garment. The pouch converges to a generally pointed lower end and has an open upper end for receiving the cup. The open upper end is closable by gripping strips so that the cup is held in place on the wearer over the groin region. U.S. Pat. No. 2,283,684 also discloses a relatively rigid cup member which is inserted in a pouch that is worn around the waist of the wearer to position the cup member over and in contact with the groin region.

It is also known, as disclosed in the U.S. Pat. No. 3,176,686 to integrally connect a cup protector to elastic straps to maintain the cup in a desired position on the wearer's body. In this device the elastic straps and protector can be constructed for wear by both males and females to provide the desired bodily protection from inadvertent blows directed to the body.

U.S. Pat. No. 3,314,422 discloses a protective cup fabricated from foam rubber padding and held in place on the wearer by strap means connected to the cup. In the alternative, the cup may be used as either an undergarment or formed as an integral part of an outer garment. In this manner the cup, a cup supporter and the outer garment are all integrally combined to form one complete garment.

One of the more commonly known methods of holding a protective cup against the wearer's body to protect the groin region from impact blows is disclosed in the U.S. Pat. No. 4,134,400. This device utilizes a jock strap that includes a pouch for holding the protective cup over the groin region. The pouch is closed at one end where it is connected to straps that extend downwardly from the waistband and is open at an upper end where the inner layer of the pouch is connected to the waistband. Fasteners positioned at the opening of the pouch close the pouch to secure the cup in the pouch in position on the body.

While it has been suggested by the prior art devices to utilize jock straps to provide bodily support during athletic activity and cup protectors to provide bodily protection while participating in contact sports and sports utilizing projectiles, the known devices are specifically constructed for either one of these two types of use. Consequently, the protective devices are not adaptable for more than a single use. Separate athletic garments must be used for protection in the non-contact sports and the contact sports. Thus a jock strap that is used for support while participating in light athletic activity is not adaptable to support a protective cup to be used in contact athletic activity. Also, the known devices, as illustrated in U.S. Pat. No. 4,134,400, for supporting a protective cup on the wearer's body is not operable to provide bodily support without the protective cup.

Therefore, there is need for a multi-purpose athletic supporter that is usable in one application as means for providing bodily support while participating in rigorous work or non-contact sports and in a second application for holding a protective cup in contact with the area of the body to be protected from impact blows while participating in contact sports.

SUMMARY OF THE INVENTION

In accordance with the present invention there is provided a protective support device that includes a waistband with a pair of straps each attached at one end to the waistband. A protective enclosure is connected at one end to the opposite ends of the straps and at the opposite end to the waistband. The protective enclosure includes an inner layer and an outer layer positioned in overlying relationship. The inner layer forms a pouch. The protective enclosure has a closed lower end portion and an open upper end portion. Resilient means connects the outer layer to the waistband and provides access into the protective enclosure through the open upper end portion. The resilient means is arranged upon expansion of the waistband to draw the inner and outer layers into position closing the protective enclosure open upper end portion.

The protective device when worn is positioned with the pouch in contact with the groin region of the body to provide bodily support. In this position, the inner and outer layers are urged into substantially overlying, abutting relation with the resilient means engaging the waistband to maintain the upper end of the protective enclosure closed. Preferably, the resilient means is fabricated of an elastic material. The elastic material is movable between a stretched position to close the open upper end portion and an unstretched position to permit access into the protective enclosure through the open upper end portion.

The protective enclosure is constructed to hold a protective insert in supporting relation with the groin region of the body. The resilient means when stretched into abutting relation with the waistband upon expansion of the waistband closes the open upper end portion to securely retain the protective insert in the protective enclosure. The protective insert is a groin protector, such as a cup fabricated preferably of molded plastic. Thus, the protective support device can be worn in one application without the protective insert to provide bodily support of the groin region by the pouch formed by the protective enclosure, and in a second application with a cup protector positioned in the protective enclosure and held in contact with the groin to protect against impact blows.

The resilient means is preferably an elastic strap having opposite end portions secured to the waistband. The elastic strap is secured intermediate the opposite end portions to the protective enclosure outer layer to thereby support the protective enclosure from the waistband. The elastic strap is expandable with the waistband and movable into abutting relation with the waistband to close the open upper end portion of the protective enclosure. Thus, when the protective support device is worn with or without a protective insert, the elastic strap is stretched to close the opening into the protective enclosure.

The inner and outer layers of the protective enclosure are sewn together to form the closed lower end portion and along the lateral edges. The outer layer has an upper edge connected to the elastic strap and is expandable with the elastic strap from a position closing the open upper end portion to a position permitting access into the protective enclosure through the open upper end portion. The inner layer has an upper edge connected to the waistband in underlying relation with the outer layer. The inner layer is preferably elastic mesh material which forms the pouch held in contact with the groin region to provide bodily support.

Accordingly, the principal object of the present invention is to provide an athletic protective support device operable to provide groin protection with or without a protective cup.

Another object of the present invention is to provide an athletic supporter that can be worn in one application without a protective cup to provide bodily support and in another application with a protective cup to protect against impact blows.

A further object of the present invention is to provide an athletic supporter having an enclosure for receiving a protective cup where the enclosure is connected to the waistband of the supporter and functions in one application without a protective cup to provide bodily support and in a second application with a protective cup which is retained in an operative position in the enclosure to provide impact protection.

These and other objects of the present invention will be more completely disclosed and described in the following specification, the accompanying drawings, and the appended claims.

DESCRIPTION OF THE PREFERRED EMBODIMENT

Figure 1:
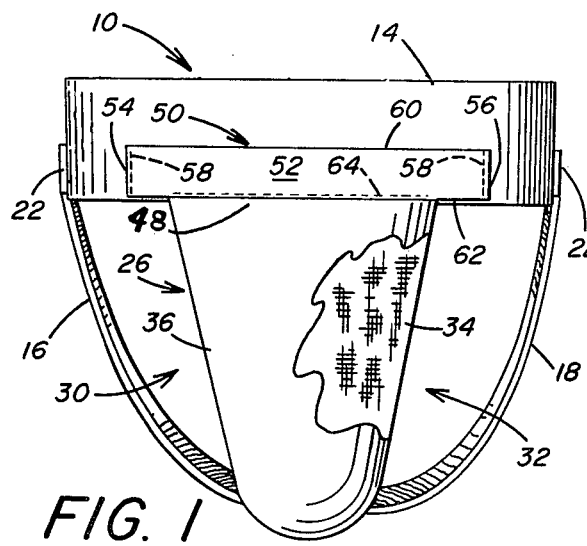
FIG. 1 is a front view of a protective support device, illustrating a protective enclosure formed by inner and outer layers of elastic mesh material connected to an elastic waistband.
Figure 2:
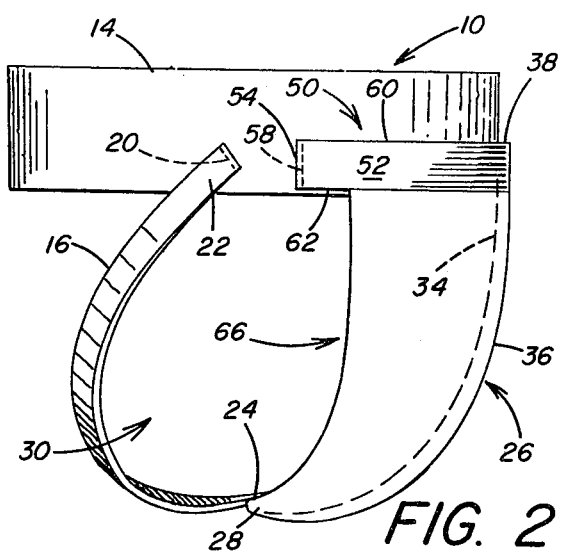
FIG. 2 is a view in side elevation of the protective support device, illustrating the protective enclosure connected at a lower end to leg straps and at an upper end to the waistband and an expandable strap.
Figure 3:
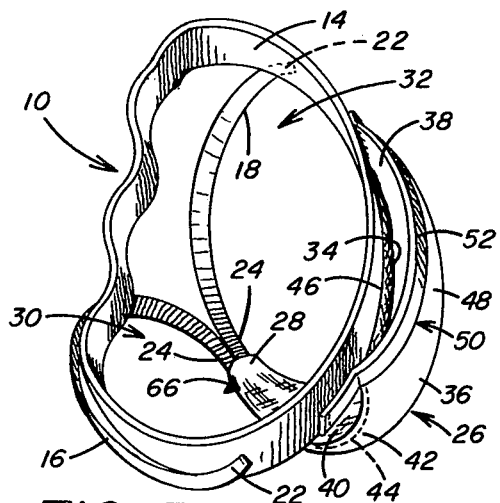
FIG. 3 is a perspective top plan view of the protective support device, illustrating an opening into the protective enclosure for receiving a protective cup.
Figure 4:
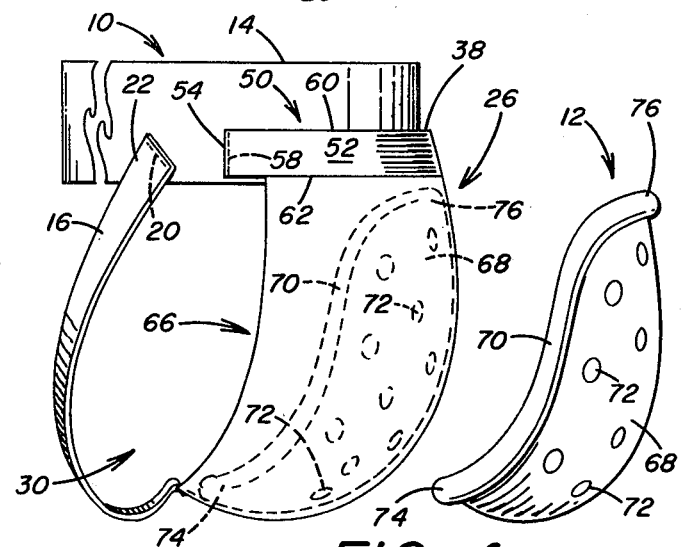
FIG. 4 is a view in side elevation of a protective cup and the protective support device, illustrating the protective cup in phantom in an operative position within the protective enclosure.
Figure 5:
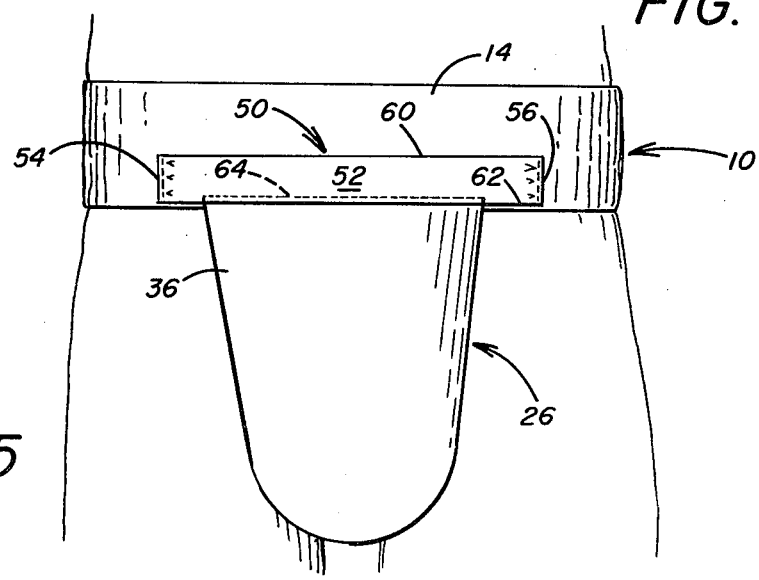
FIG. 5 is a schematic representation of the manner in which the protective support device of the present invention is worn where expansion of the waistband stretches the elastic strap across the protective enclosure to close the open upper end portion thereof.

Referring to the drawings and particularly to FIGS. 1–3, there is illustrated a multi-purpose athletic supporter or jockstrap generally designated by the numeral 10 that is adaptable to be worn with or without a protective insert, generally designated by the numeral 12 in FIG. 4, in accordance with the type of athletic activity for which the athletic supporter is to be worn. The athletic supporter 10 includes an elastic waistband 14, which as illustrated in FIG. 5 is operable to be worn securely around the waist of the wearer. A pair of leg straps 16 and 18 are attached by stitching 20 at ends 22 to opposite sides of the waistband 14. The straps 16 and 18 extend downwardly in a looped fashion and are connected at opposite ends 24 to a protective enclosure generally designated by the numeral 26 at a closed lower end portion 28 thereof as seen in FIG. 3.

The waistband 14 together with the straps 16 and 18 and the protective enclosure 26 form openings generally designated by the numerals 30 and 32 for receiving the leg of the wearer. In this manner, the straps 16 and 18 and the waistband 14 securely engage the lower torso of the wearer to hold the protective enclosure 26 in contact with the groin area of the wearer to provide bodily support while participating in athletic activities. The strap end portions 24 are connected to the enclosure lower end portion 28 in a suitable manner as by stitching.

The protective enclosure is formed by an inner layer 34 of elastic mesh material and an outer 36 of elastic mesh material. The inner and outer layers 34 and 36 are connected to form the protective enclosure 26 having the closed lower end portion 28 and an open upper end portion 38. To form the protective enclosure 26, lateral edges 40 and 42 of inner and outer layers 34 and 36 are positioned in overlying, abutting relation and sewn together along a seam 44, as illustrated in FIG. 3.

The inner layer 34 of elastic mesh material has an upper edge 46 which is secured by stitching to the waistband 14. The outer layer 36 of elastic mesh material has an upper edge 48 which is connected along its length to a resilient device generally designated by the numeral 50 operable to provide access into the protective enclosure 26 through the open upper end portion 38 thereof. With this arrangement the inner and outer layers 34 and 36 of elastic mesh material are positioned in overlying relationship and are connected at the adjacent edge portions thereof except at the open upper end portion 38 of the protective enclosure 26.

The resilient device 50 is preferably an elastic strap 52 having opposite end portions 54 and 56, as illustrated in FIG. 1, that are secured by stitching 58 to the waistband 14. The elastic strap 52 has an upper edge 60 which is movable into and out of abutting relation with the oppositely positioned portion of the waistband 14. With this arrangement the open upper end portion 38 into the protective enclosure 26 is closed when the waistband 14 is stretched when worn, as illustrated in FIG. 5. The elastic strap 52 also includes a lower edge 62 which is suitably connected by stitching 64, as illustrated in FIG. 1, to the upper edge 48 of the outer layer 36 of elastic mesh material. Thus the intermediate portion of the elastic strap 52 is movable toward and away from the waistband 14.

With this arrangement, the outer layer 36 of elastic mesh material is movable relative to the inner layer 34 of elastic mesh material and the waistband 14. The elastic strap 52 is movable from a position closing the protective enclosure 26 to a position permitting access into the protective enclosure 26 through the open upper end portion 38. The inner layer 34 of elastic mesh material being connected to the waistband 14 in underlying relation with the outer layer 36 of elastic mesh material forms a pouch generally designated by the numeral 66 in FIG. 3.

The protective support device 10 is thus worn with the pouch 66 formed by the overlying inner and outer layers 34 and 36 in contact with a wearer's body to provide support for the groin region. This permits the protective support device 10 to be worn without the protective insert 12 to provide bodily support. In this manner, the protective support device 10 is worn without the insert 12 for gym-type athletic activities that do not involve bodily contact or use of a projectile.

To facilitate use of the athletic supporter 10 without the protective insert 12, the inner layer 34 forming the pouch 66, as stated above, is fabricated of an elastic mesh material. Being of an elastic mesh material, the inner layer 34 is then movable between a stretched condition and an unstretched condition so as to securely hug the groin region of the wearer and provide bodily support without the presence of the protective insert 12 in the protective enclosure 26. Thus when the protective enclosure 26 is empty, the inner layer 34 is positioned in contact with the groin region of the wearer's body to provide the desired bodily support for participation in rigorous work or gym-type athletic activity.

The protective enclosure 26 formed by the inner and outer layers 34 and 36 of elastic mesh material is constructed, as above described, to hold the protective insert 12 in impact protective relation with a body for use of the athletic supporter in activities where greater groin protection is required particularly for the contact sports and the sports involving projectiles. The protective insert 12 is preferably a conventional protective cup 68 as illustrated in FIG. 4.

The cup 68 is generally fabricated of molded plastic which is shatterproof. The cup 68 is contoured to be positioned on the wearer to protect the groin region and includes an outer peripheral edge 70 of foam padding. The body of the cup 68 also includes apertures 72 to provide circulation of air therethrough. The insert 12 is removably received in the protective enclosure 26 of the athletic supporter 10.

To position the insert 12 in the enclosure 26, the lower end portion 74 of the cup 68 is first advanced through the enclosure open upper end portion 38 between the inner and outer layers 34 and 36. The lower end portion is extended downwardly through the enclosure 26 until it reaches the closed end portion 28 of the enclosure 26. When the cup 68 is in the desired position within the enclosure 26, the upper end portion 76 of the cup 68 is positioned below the elastic strap 52 as illustrated in FIG. 4.

The cup 68 is easily inserted within the enclosure 26 by stretching the elastic strap 52 away from the waistband 14 to enlarge the opening into the upper end portion 38. The strap 52 is stretched to the extent to permit the cup 68 to be advanced through the open upper end portion 38 and into position between the inner and outer layers 34 and 36 in the enclosure 26. Once the cup 68 is in position in the enclosure 26, the elastic strap 52, as well as the inner and outer layers 34 and 36 are tensioned to maintain the cup 68 in the desired position covering the groin area of the wearer.

After the cup 68 is positioned in the enclosure 26 of the athletic supporter 10 the elastic strap 52 serves to lock the cup in place within the enclosure 26. The locking action is accomplished by stretching of the elastic strap 52 upon expansion of the waistband 14 around the waist of the wearer. When the waistband 14 stretches the elastic strap 52 stretches with it. The elastic strap 52 when stretched with the waistband 14 moves into abutting relation with the waistband 14 thereby closing the open upper end portion 38 of the protective enclosure 26.

When the athletic supporter 10 is worn with the cup 68 in the protective enclosure 26, the enclosure 26 is self-locking by expansion of the elastic strap 52 to retain the cup 68 in the desired position in the enclosure 26. This assures that during athletic activity the cup 68 is held in position to protect the groin area. Due to the elastic nature of the inner and outer layers 34 and 36 and the elastic strap 52 the cup 68 will not become displaced from the desired position in the enclosure 26 as a result of bodily movement of the wearer.

Thus with the present invention, the athletic supporter 10 can be worn without a protective insert 12 to provide bodily support by the pouch 66, formed by the layers 34 and 36, in contact with the groin region of the wearer. In addition when it is desired to protect the groin region against impact blows, the athletic supporter 10 can be worn with the protective insert 12. This solves the problems of having to maintain one supporter strictly for use in gym-type sports and a second supporter strictly for use with a protective cup when participating in contact sports and sports involving projectiles. Thus the athletic supporter 10 of the present invention can be used with or without the protective insert 12. When used with the protective insert 12, the insert or cup is easily positioned and retained in the protective enclosure 26 without the need for fasteners or the like.

According to the provisions of the Patent Statutes, we have explained the principle, preferred constuction and mode of operation of our invention and have illustrated and described what we now consider to represent its best embodiments. However, it should be understood that, within the scope of the appended claims, the invention may be practiced otherwise than as specifically illustrated and described.

We claim:

1. A multi-purpose protective athletic support garment for use with and without a protective cup comprising, an elastic waistband, a pair of leg straps having upper end portions secured to said waistband, said pair of leg straps having lower end portions, an inner layer of elastic material connected at one end to said lower end portions of said leg straps and at the opposite end to said waistband, an outer layer of elastic material positioned in overlying relationship with said inner layer of elastic material, said outer layer of elastic material connected at one end to said lower end portions of said leg straps, said inner layer and said outer layer having lateral edges positioned in overlying relation, said lateral edges being connected to each other, said outer layer having an upper edge positioned in overlying abutting relation with said waistband to form a pouch, said pouch being positioned in contact with the groin region of a wearer's body to provide protection for the groin region, a protective cup removably insertable in said pouch to provide the wearer with additional groin protection, an elastic pouch closure strap having opposite end portions and an intermediate portion therebetween, said closure strap end portions being secured to said waistband, said closure strap intermediate portion being secured to said outer layer upper edge to support said pouch from said waistband, said closure strap intermediate portion positioned in overlying abutting relation with said waistband for movement relative to said waistband to close said pouch, said pouch having an upper end portion at said waistband and a closed end portion at the connection of said inner and outer layers to the opposite ends of said straps, said pouch closure strap and said outer layer upper edge being movable into and out of abutting relation with said waistband from a first position closing said pouch by abutting contact of said pouch closure strap intermediate portion with said waistband to retain said protective cup in said pouch to a second position permitting access into said pouch by displacement of said pouch closure strap intermediate portion from contact with said waistband to insert and remove said protective cup for use of said pouch to provide groin protection with and without said protective cup in said pouch, and said pouch closure strap being stretched upon expansion of said waistband around the waist of a wearer to move into abutting relation with said waistband to close said pouch upper end portion so that said pouch is self-locking by expansion of said waistband with and without said protective cup being positioned in said pouch.

2. A multi-purpose protective athletic support garment as set forth in claim 1 in which, said pouch without said protective cup therein is positioned in contact with the body of the wearer to provide groin protection, and said inner and outer layers being urged into substantially overlying, abutting relation when said pouch closure strap engages said waistband to maintain said pouch in a closed position.

3. A multi-purpose protective athletic support garment as set forth in claim 1 in which, said pouch is positioned in supporting relation with the groin area of the wearer to provide bodily support with and without said protective cup in said pouch, and said pouch being stretchable to receive and maintain said protective cup in position to protect the groin area of the wearer against impact blows.

4. A multi-purpose protective athletic support garment as set forth in claim 1 in which, said inner layer is fabricated of an elastic mesh material movable between a stretched condition and an unstretched condition, and said inner layer being operable when said pouch is empty to be positioned in contact with a wearer's body to provide groin protection.

5. A multi-purpose protective athletic support garment as set forth in claim 1 in which, said inner layer has an upper edge connected to said waistband in underlying relation with said outer layer upper edge, said inner layer being held in contact with a region of a wearer's body to provide bodily support, and said outer layer being movable toward and away from said inner layer to permit access to said pouch through said pouch upper end portion.

* * * * *